US009579527B2

(12) United States Patent
Vic et al.

(10) Patent No.: US 9,579,527 B2
(45) Date of Patent: Feb. 28, 2017

(54) COSMETIC CARE OR MAKEUP COMPOSITION CONTAINING POWDERS AND MANUFACTURING PROCESS

(75) Inventors: Sabine Vic, Semoy (FR); Philippe Ferrand, Checy (FR); Eric Perrier, Les Cotes d'Arey (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 13/222,560

(22) Filed: Aug. 31, 2011

(65) Prior Publication Data

US 2012/0308499 A1 Dec. 6, 2012

(30) Foreign Application Priority Data

May 31, 2011 (FR) ...................................... 11 54739

(51) Int. Cl.
| | |
|---|---|
| *A61K 8/90* | (2006.01) |
| *B29B 9/12* | (2006.01) |
| *A61Q 1/10* | (2006.01) |
| *A61Q 1/02* | (2006.01) |
| *A61Q 1/12* | (2006.01) |
| *A61Q 1/08* | (2006.01) |
| *B29C 39/02* | (2006.01) |
| *B29C 71/00* | (2006.01) |
| *A61K 8/25* | (2006.01) |
| *A61K 8/31* | (2006.01) |
| *A61K 8/34* | (2006.01) |

(52) U.S. Cl.
CPC ............... *A61Q 1/12* (2013.01); *A61K 8/25* (2013.01); *A61K 8/31* (2013.01); *A61K 8/345* (2013.01); *A61K 8/90* (2013.01); *A61Q 1/10* (2013.01)

(58) Field of Classification Search
None
See application file for complete search history.

(56) References Cited

U.S. PATENT DOCUMENTS

| | | | |
|---|---|---|---|
| 4,648,908 A * | 3/1987 | Takasuka ................ A61K 8/11 106/417 |
| 6,437,068 B2 | 8/2002 | Loffler et al. | |
| 6,652,844 B1 | 11/2003 | Arseguel et al. | |
| 2005/0037038 A1 | 2/2005 | Gupta et al. | |
| 2005/0249684 A1 | 11/2005 | Dobkowski et al. | |
| 2005/0276776 A1* | 12/2005 | Liechty et al. ............ 424/70.12 |
| 2006/0013790 A1* | 1/2006 | Shimizu ..................... 424/70.12 |
| 2007/0166337 A1* | 7/2007 | Treudler .............. A61K 8/0208 424/401 |
| 2009/0035243 A1 | 2/2009 | Czarnota et al. | |
| 2009/0142382 A1* | 6/2009 | Shah et al. ................... 424/401 |
| 2011/0265689 A1 | 11/2011 | Schumacher et al. | |

FOREIGN PATENT DOCUMENTS

| | | |
|---|---|---|
| DE | 10 2009 037 934 | 2/2011 |
| EP | 0165137 | 12/1985 |
| EP | 0968705 | 1/2000 |
| EP | 1116733 | 7/2001 |
| EP | 1216693 | 6/2002 |
| EP | 1776986 | 4/2007 |
| EP | 1977729 | 10/2008 |
| FR | 2 779 960 | 12/1999 |
| WO | WO 03/022236 | 3/2003 |
| WO | WO 2005/070354 | 8/2005 |

OTHER PUBLICATIONS

English Translation of Japanese Patent Document No. 2006-160616.*
JP 63135312 (English Translation of Abstract).*

* cited by examiner

*Primary Examiner* — Robert A Wax
*Assistant Examiner* — Randeep Singh
(74) *Attorney, Agent, or Firm* — Hamre, Schumann, Mueller & Larson, P.C.

(57) ABSTRACT

The invention relates to a solid cosmetic composition, in the form of a loose or compact powder, comprising:
  (a) from 50% to 99% by weight of at least one particulate solid phase,
  (b) from 0.5% to 50% by weight of at least one non-volatile liquid phase, and
  (c) from 0.01% to 4% by weight of at least one block copolymer obtained from a first monomer of 2-acrylamidomethylpropanesulphonic acid and from a vinyl second monomer having a nitrogenous cyclic side chain.

The invention also relates to a process for manufacturing such a composition, which comprises:
  (i) mixing the particulate solid phase, the non-volatile liquid phase, the block copolymer and water so as to obtain a slurry,
  (ii) suctioning off the water present in the slurry so as to obtain a dry powder.

6 Claims, No Drawings

COSMETIC CARE OR MAKEUP COMPOSITION CONTAINING POWDERS AND MANUFACTURING PROCESS

The invention relates to a powder-based composition, particularly intended for cosmetic care of and/or making up the skin. This composition contains a filler- and pigment-based particulate solid phase, a non-volatile liquid phase and a particular polymer.

PRIOR ART

Powder-based cosmetic products for making up and/or caring for the face and the body may be loose powders or compact powders.

Powder-based cosmetic compositions, whether said powders are loose or compact, can be prepared via the "dry" process or via the "wet" process if a solvent or a diluent is used to disperse the powders. Via the dry process, the pulverulent materials such as the fillers and the pigments are mixed with a binder essentially composed of non-volatile fatty substances. Via the wet process, the pulverulent materials and the binder are diluted in a solvent in order to obtain a slurry which is then dried.

A loose powder is generally prepared dry by simple mixing of the ingredients, optionally accompanied by milling and/or screening.

Compact powders are generally prepared by mixing all the components of the pulverulent phase and then adding a binding fatty phase to this mixture with stirring. The mixture is then milled, screened, and then poured into a dish and compacted. The compacting is typically carried out at a pressure of from 5 to 25 MPa.

A compact powder is different from a "cast" composition, which is prepared by heating a fatty phase that is solid at ambient temperature and that needs to be melted in order for it to be mixed with pulverulent materials. Compact powders have, compared with cast compositions, a better ability to crumble when the composition is taken up for the purpose of applying it to the skin.

There are also compact powders produced by the wet process of which the production process uses a slurry and does not comprise a dry compacting step.

For example, the "cast-baked" method consists in diluting the powders in a solvent at ambient temperature in order to prepare a slurry, in depositing obtained pieces of the slurry on a ceramic plate, and then in baking the product in an oven. The dried powder cakes are then worked into the shape of the casing which must serve as packaging. The ceramic support to which the powder cake adheres remains connected to the composition with which it is therefore packaged.

Another method consists in casting the slurry into moulds, and then in removing the solvent contained in the slurry, for example, by suction, by pressing or by means of an absorbent material.

It is often difficult to obtain cosmetic powders of good quality since many criteria—such as their sensory properties, their care or makeup performance levels, and their cohesion—must be taken into account. In addition, the improvement in certain criteria often occurs at the expense of others. For example, better crumbling often results in a lack of cohesion of the powder. Better creaminess often results in a compact that is less practical for the user because of a considerable risk of poor take-up at the surface, said surface having a strong tendency to become waxy or to patinate.

The properties desired for obtaining a cosmetic product of good quality include, in particular, the covering capacity, the adherence, the capacity to absorb moisture and sebum from the skin, the spreading capacity, the softness, the fineness, the comfort on the skin, a long staying power on the skin, the uniformity, storage-stability, and easy take-up of the powder for the purpose of applying it.

It is also necessary to obtain good cohesion of the powder, which can be reflected, for example, by good resistance of the powders to mechanical impacts and to heat shocks, when said powders are compact, or by less volatility when the powders are used and/or better staying power of the powders on the skin, when said powders are loose.

The resistance of compact powders to mechanical impacts and/or to heat shocks is often insufficient, which causes the breaking up of the product or degradation of the product during transport to the place of sale. The product user may also inadvertently drop the product from a significant height.

PURPOSE OF THE INVENTION

The present invention aims to propose novel powder-based cosmetic compositions which improve the properties of the prior art powders, and which improve in particular the resistance to mechanical impacts and heat shocks, the comfort of the powder on the skin, the staying power of the powder on the skin, or all these properties simultaneously.

The purpose of the invention is also to solve the technical problem which consists in providing a compound of powder which is uniform.

The purpose of the invention is also to simplify the current industrial processes by proposing a single composition allowing greater manufacturing flexibility. This composition makes it possible in particular to obtain various final forms of powders and thus to reduce the number of production lines.

The purpose of the invention is to solve the technical problems reliably and reproducibly and in a way that can be used on the industrial scale, in particular in the cosmetics industry.

DESCRIPTION OF THE INVENTION

Thus, the present invention relates to a cosmetic composition in solid form, in particular in the form of a loose or compact powder, comprising:

(a) from 50% to 99% by weight, preferably from 70% to 90% by weight, of at least one particulate solid phase, (b) from 0.1% to 50% by weight, preferably from 5% to 30% by weight, of at least one non-volatile liquid phase, and (c) from 0.01% to 4% by weight, preferably from 0.05% to 2% by weight, of at least one block copolymer obtained from an acrylamide first monomer bearing a sulphonic group and from a vinyl second monomer having a nitrogenous side chain.

In one embodiment, the sum of weight percentages of the particulate solid phase, the non-volatile liquid phase and the block copolymer equals 100%. The composition according to the invention has at least one of the following advantages compared with the prior art powders: its shiny appearance is more attractive for sale, its sensory properties are improved, its stability during storage is better, its cohesion when it is handled is improved, its makeup performance levels are improved. In certain embodiments, all these advantages can be obtained simultaneously.

More specifically, the composition according to the invention can have the advantage of being less fragile and more stable than the prior art powders when it is taken up by the user or when it is subjected to impacts or shocks. The applicant has found, unexpectedly, that the block copolymer makes it possible to reinforce the cohesion and the stability of the composition.

The sensory properties of the composition of the invention can also be improved. In particular, in the case of compositions comprising pearlescent agents, the surface of the composition as observed by a user is shinier than the surface of the prior art powders.

The fatty binders used to agglomerate the powders have a tendency to render the surface of the compacted product matt. However, entirely unexpectedly, the applicant has observed that the composition of the invention can contain very high amounts of fatty binders without the texture taking on a matt or waxy appearance. Increasing the amount of fatty binders makes it possible to increase the feeling of softness, or even of creaminess, of the composition when it is taken up with the finger or applied to the skin. The composition of the invention therefore has a shinier appearance than the prior art powders that have an equivalent creaminess.

The applicant has also found that the composition can contain amounts of binder that are lower than those normally necessary for guaranteeing the cohesion of the powder. In certain embodiments, the amount of fatty binder is less than 0.1% by weight.

The composition applied to the skin, for example the eyelids or the cheeks, can provide a greater feeling of comfort than those of the prior art powders.

The staying power of the composition on the skin can also be improved. In particular, the pearlescent agents and the glitter flakes that are contained in the composition remain on the skin for a longer period of time. This improved staying power can be reflected by better staying power with respect to rubbing and/or better water resistance. The improvement in the staying power is particularly appreciable and advantageous for the formulation of compositions applied to the eyelids, such as eye shadows, because they undergo repeated rubbing owing to the natural mobility of the eyelids.

The composition contains a block copolymer obtained from an acrylamide first monomer bearing a sulphonic group and a vinyl second monomer having a nitrogenous side chain.

According to one embodiment, the block copolymer gels in the presence of water. It preferably has a viscosity, measured at 1% in distilled water, of between 40 000 and 70 000 mPa·s.

The first monomer is preferably a 2-acrylamidomethylpropanesulphonic acid salt. The sulphonic acid group of the first monomer is preferably in the form of an ammonium or sodium salt.

The second monomer is preferably nonsalifiable. It may be a vinyl monomer having a nitrogenous cyclic side chain or a vinyl monomer having an amide function, for instance N-vinylpyrrolidone.

A preferred block copolymer may be a copolymer of the ammonium salt of 2-acrylamidomethylpropanesulphonic acid and N-vinylpyrrolidone, such as the product sold under the name Aristoflex® AVC by the company Clariant. The block copolymer may bear the INCI name Ammonium Acryloyldimethyltaurate/VP Copolymer or correspond to the CAS reference number 335383-60-3. Another block copolymer that can be used in the composition of the invention may be a copolymer of the sodium salt of 2-acrylamidomethylpropanesulphonic acid and N-vinylpyrrolidone, such as the product sold under the name Aristoflex® AVS by the company Clariant. The block copolymer may bear the INCI name Sodium Acryloyldimethyltaurate/VP Crosspolymer.

The composition preferably contains from 0.05% to 2% by weight, more preferably from 0.1% to 0.4% by weight, of the block copolymer.

The particulate solid phase advantageously consists of a mixture of pulverulent materials comprising at least one pigment and/or at least one filler.

The pigments may be chosen from mineral pigments, organic pigments and pearlescent pigments.

The mineral pigments may be chosen from iron oxides, in particular black, yellow, red and brown iron oxides; manganese violet; ultramarine blue; chromium oxides, in particular chromium oxide hydrate, Prussian blue, carbon black, and mixtures thereof.

Among the organic pigments, mention may in particular be made of the lakes obtained from dyes such as the dyes D&C Black No. 2, FD&C Blue No. 1, FD&C Green No. 3, D&C Green No. 5, D&C Orange No. 4, D&C Orange No. 5, D&C orange No. 10, D&C No. red 3, D&C Red No. 6, D&C Red No. 7, D&C red No. 9, D&C red No. 13, D&C red No. 19, D&C Red No. 21, D&C Red No. 22, D&C Red No. 27, D&C Red No. 28, D&C Red No. 30, D&C Red No. 33, D&C Red No. 36, FD&C Red No. 40, FD&C Yellow No. 5, FD&C Yellow No. 6, D&C Yellow No. 10 and cochineal carmine.

The pearlescent pigments are, for example, chosen from mica coated with titanium oxide, titanium-mica coated with iron oxide, titanium-mica coated with Prussian blue, titanium-mica coated with chromium oxide, titanium-mica coated with an organic pigment as described above, and also pigments based on bismuth oxychloride.

The filters may be mineral or organic, and of any shape, platelet-shaped, spherical or oblong.

The fillers are chosen in particular from inorganic fillers such as:

talc, preferably in the form of particles having dimensions of less than 40 µm;

micas of natural or synthetic origin having dimensions of from 2 to 200 µm, preferably from 5 to 70 µm, and a thickness of from 0.1 to 5 µm, preferably from 0.2 to 3 µm;

kaolin having particle sizes of generally less than 30 µm;

metal soaps derived from organic carboxylic acids containing from 8 to 22 carbon atoms, preferably from 12 to 18 carbon atoms, for example zinc stearate, magnesium stearate or lithium stearate, zinc laurate or magnesium myristate, preferably in the form of particles having dimensions of less than 10 µm;

zinc oxides, titanium oxides; calcium carbonate; magnesium carbonate, magnesium hydrogen carbonate, silica, glass beads, ceramic beads;

and mixtures thereof.

As fillers, use may also be made of organic fillers such as:

crosslinked or noncrosslinked starches, for example maize, wheat or rice starches;

crosslinked or noncrosslinked, spheronized or nonspheronized, expanded or nonexpanded powders of synthetic polymers, such as polyethylene powders, polyester powders (for example isophthalate or terephthalate), polyamide powders (for example poly-β-alanine powders and nylon powders such as those sold under the name Orgasol®), poly(meth)acrylic acid or poly(meth)acrylate powders such as crosslinked methyl methacrylate powders, polyurethane powders such as the copolymers of hexamethylene diisocyanate and of trimethylol hexyl lactone sold under the names Plastic Powder® D-400 and Plastic Powder® D-800 by the company Toshiki, divinylbenzene-crosslinked polystyrene powders, silicone resin powders such as silsesquioxanes, or tetrafluoroethylene (Téflon®) powders;

and mixtures thereof.

Advantageously, the composition of the invention may contain large proportions of spherical powders while at the same time keeping satisfactory cohesion, which is not the case for the prior art powders. This is because it is generally necessary to apply high compression forces in order to cause the particles of spherical powders to adhere to one another since they have a tendency to roll and slide over one another. The copolymer used in the composition according to the invention makes it possible to render these particles cohesive without having to compact them at a high pressure.

According to one embodiment, the composition of the invention contains spherical fillers in a content ranging from 10% to 40% by weight, relative to the total weight of the composition, preferably ranging from 15% to 35% by weight, preferentially ranging from 25% to 35% by weight.

The fillers advantageously have an average diameter of greater than 100 nm and less than 200 µm, and more particularly a diameter of between 5 and 150 µm.

According to one embodiment variant of the invention, the pigments and the fillers may be treated so as to modify their surface finish. The pigments and the fillers used may be advantageously devoid of surface treatment to render them hydrophobic or hydrophilic, while at the same time guaranteeing sufficient cohesion of the powder of the invention.

The composition of the invention contains at least one non-volatile liquid phase.

The term "non-volatile liquid phase" is intended to mean a phase comprising a non-volatile liquid, i.e. a liquid which has a vapour pressure of less than 13 Pa at atmospheric pressure (approximately 0.1 MPa) and at ambient temperature (25° C.). It is also possible to define a non-volatile liquid as having a rate of evaporation such that the amount evaporated-off after 30 minutes is less than 0.07 mg/cm$^2$ under the temperature and pressure conditions defined above.

In one embodiment, this non-volatile liquid phase contains at least one non-volatile oil. This oil is preferably the major component by weight of said phase. In another embodiment, the liquid phase is free of oil and contains in the majority a non-volatile alcohol.

For the purpose of the present invention, the term "oil" is intended to mean a compound that is liquid at ambient temperature (25° C.) and at atmospheric pressure (approximately 0.1 MPa) and that is not soluble in water at 25° C. at a concentration of at least 1% by weight relative to the weight of water.

The non-volatile oil may be chosen from those normally used in the cosmetics industry and particularly from linear or branched hydrocarbons, fatty acids which are optionally branched and/or unsaturated, fatty alcohols which are optionally branched and/or unsaturated, fatty acid and/or fatty alcohol esters or polyesters, perfluoro and/or organofluoro oils, non-volatile silicone oils, fluorosilicone oils, and mixtures thereof.

The non-volatile liquid phase may also contain a non-volatile alcohol chosen from:

C3-C5 polyols, for example a C3-C5 aliphatic diol (or glycol) such as pentylene glycol (pentane-1,5-diol), or a triol such as glycerol, a glycol ether or an aromatic alcohol such as phenoxyethanol, and mixtures thereof.

The non-volatile liquid phase preferably contains at least one liquid chosen from an oil, an alcohol chosen from C3-C5 polyols, in particular glycerol, glycol ethers, and mixtures thereof. According to one embodiment, the non-volatile liquid phase contains less than 0.1% of oil or is free of oil.

The composition of the invention may optionally comprise agents for structuring or gelling the non-volatile liquid phase, in particular pasty fatty substances or waxes, of animal, plant, mineral or synthetic origin, polyorganosiloxanes, silicone polyamides comprising siloxane units, hydrocarbon-based polyamides, homopolymers and copolymers comprising urethane and/or urea units, block copolymers and homopolymers comprising at least one sequence of styrene units or derivatives and at least one sequence of olefin units and/or derivatives.

The powder-based composition can advantageously incorporate any type of cosmetic active agents, whether they are hydrophilic or lipophilic. The preferred active agents are chosen from the group consisting of substances having an anti-ageing activity; substances having a depigmenting or a lightening activity on the skin; substances having a slimming activity; substances having a moisturizing activity; substances having a calming, soothing or relaxing activity; and mixtures thereof.

The composition may also comprise at least one excipient chosen from dyes, surfactants, fragrances, electrolytes, antioxidants, preservatives, and physical and/or chemical UV-screening agents.

The composition is advantageously devoid of surfactant, since it is not necessary, unlike the prior art powders obtained by forming a slurry of the pulverulent materials with water, to use a surfactant in order to guarantee good uniformity of the slurry. Without this embodiment being excluded, it is preferred for the composition of the invention not to contain a surfactant chosen from optionally polyethoxylated sorbitan esters, fatty acid esters of glycerol, fatty acid esters or polyesters of sucrose, fatty acid esters of polyethylene glycol, polyether-modified polysiloxanes, fatty alcohol ethers of polyethylene glycol, alkylpolyglycosides and hydrogenated lecithin.

The composition of the invention may have various cosmetic uses, and in particular may serve as a foundation, a complexion base, a body makeup powder, a care powder, a face makeup powder, a blusher or face powder, an eyeshadow, a complexion illuminator, an antisun powder, or a protective complexion powder. The composition of the invention is preferably an eyeshadow or a face powder.

The application of the powders can be carried out with a brush, with a sponge or with a finger.

According to another aspect, the invention relates to the use of a block copolymer as defined above for improving the cohesion of a powder. In the case of a compact powder, the improvement in its cohesion can be reflected by better resistance to mechanical impacts and/or better resistance to heat shocks. In the case of a loose powder, the improvement in its cohesion can be reflected by a lower volatility and better staying power on the skin. A powder will be "volatile" when it has a tendency to scatter into the air at the time it is taken up with a brush or at the time it is applied to the skin. The improvement in the cohesion of the loose powder may also be reflected by better attachment of the pulverulent materials constituting the powder, such as the glitter flakes, which sometimes have a tendency to detach from the skin over time after application of the composition. According to yet another aspect, the invention relates to the use of a block copolymer as defined above for improving the staying power of a powder-based composition on the skin.

The powder-based composition of the invention can be produced by the wet process by preparing a slurry (or pasty composition) according to an appropriate industrial process. It can also be produced by the dry process.

A subject of the invention, according to one of its aspects, is a process for manufacturing the powder-based composition described above, which process comprises:

(i) mixing the particulate solid phase, the non-volatile liquid phase, the block copolymer and a volatile liquid so as to obtain a slurry, (ii) placing it in a mould, and (iii) removing said volatile liquid present in the slurry.

The process of the present invention makes it possible to advantageously obtain a homogeneous slurry and homogeneous dry compositions. The term "homogeneous" is intended to mean a composition of which the various constituents are distributed so as to give a uniform or substantially uniform appearance to the naked eye. A composition in slurry form is homogeneous, for example, when it comprises only one phase, and does not comprise lumps, i.e. solid particles or solid agglomerates of poorly dispersed materials. It is not necessary to mill the slurry in order to obtain good dispersion of the ingredients, unlike certain prior art processes.

The pasty composition of the invention is very advantageous since it can be used to manufacture a powder-based composition, irrespective of the final form desired; compact or loose.

The process according to the invention generates less industrial waste since it is not necessary to work the powder cakes as in a "cast-baked" process.

The pasty composition containing the mixture of the particulate solid phase, of the non-volatile liquid phase, of the block copolymer and of the volatile liquid can be advantageously used in any conventional wet process for preparing powders known to those skilled in the art.

A subject of the invention, according to another of its aspects, is a process for manufacturing a powder-based composition, which process comprises:

(i) dispersing, in water, a particulate solid phase, a non-volatile liquid phase, and an ionic block copolymer obtained from a first monomer of a 2-acrylamidoalkylsulphonic acid salt and from a second monomer, so as to obtain a slurry, (ii) placing it in a mould, and (iii) removing the water present in the slurry by suctioning off under vacuum, followed by drying at a temperature of less than 70° C.

The first monomer may be 2-acrylamidomethylpropanesulphonic acid or a salt thereof, such as an ammonium or sodium salt.

The second monomer may be chosen from (meth)acrylic acid, (meth)acrylates, (meth)acrylamides, (meth)acrylate salts, and vinylpyrrolidone, and derivatives thereof.

The block copolymer may be, for example, a block copolymer of a 2-acrylamidomethylpropanesulphonic acid salt and of N-vinylpyrrolidone, such as the product sold under the name Aristoflex® AVC or the name Aristoflex® AVS by the company Clariant, a copolymer of a 2-acrylamidomethylpropanesulphonic acid salt and of an acrylate salt, such as the products sold under the references Simulgel EG® and Creagel EZ®.

The copolymer may have one of the following INCI names:

Sodium Acrylate/Sodium Acryloyldimethyltaurate Copolymer,

Sodium Acryloyldimethyltaurate/VP Crosspolymer,

Acrylamide/Sodium Acryloyldimethyltaurate Copolymer, or

Ammonium Acryloyldimethyltaurate/VP Copolymer.

The slurry can be obtained by mixing the particulate solid phase, the non-volatile liquid phase, the block copolymer and a volatile liquid. The term "volatile liquid" is intended to mean a liquid which has a vaporization temperature of less than or equal to 110° C. at atmospheric pressure (approximately 0.1 MPa or 1 bar). A volatile liquid can also be defined as a liquid which has a vapour pressure of less than 13 Pa at atmosphere pressure (approximately 0.1 MPa) and at ambient temperature (25° C.). A volatile liquid can also be defined as a liquid having a rate of evaporation such that the amount evaporated-off after 30 minutes is greater than 0.07 $mg/cm^2$ under the temperature and pressure conditions defined above.

Advantageously, the volatile liquid is chosen from: water; a C2-C5 alcohol, preferably chosen from aliphatic monoalcohols; a water/C2-C5 alcohol mixture; a C3-C6 aliphatic diol (or glycol), such as propane-1,2-diol (or propylene glycol), propane-1,3-diol, a butylene glycol, a polyethylene glycol, or dipropylene glycol; an isoparaffin, such as isododecane or isohexadecane; a cyclic silicone oil, such as tetra-, penta- or hexacyclomethicone, or a linear silicone oil such as a dimethicone having, for example, a viscosity of 0.65 to 5 centistokes; C1-C5 fluoroalkanes; fluorosilicone oils, such as fluoroalkyldimethylsiloxanes; and any mixture thereof.

According to one embodiment, the volatile liquid contains a dispersant for the block copolymer.

According to another aspect of the invention, the volatile liquid contains water, preferably in an amount sufficient to gel the block copolymer. According to one embodiment, the volatile liquid is water or a water/C2-C5 alcohol mixture, and the copolymer is a block copolymer of a 2-acrylamidomethyl-propanesulphonic acid salt and of N-vinylpyrrolidone.

The slurry comprises the various constituents preferably in the following proportions:

from 15% to 80% by weight, relative to the total weight of the composition, of the particulate solid phase;

from 20% to 70% by weight, relative to the total weight of the composition, of the volatile liquid;

0.1% to 30% by weight, relative to the total weight of the composition, of non-volatile liquid phase, 0.01% to 2% by weight, relative to the total weight of the composition, of block copolymer.

The volatile liquid preferably represents from 25% to 60% by weight, preferably from 25% to 35% by weight, of the pasty composition.

The volatile liquid, the non-volatile liquid phase and the copolymer are preferably mixed in a first step, at a temperature of about 25° C., with stirring in a mixer known to those skilled in the art, before adding the fillers and the pigments.

The slurry can be placed in moulds in order to undergo forming according to a technique known to those skilled in the art.

The moulds may be made of metal or silicone and be reusable once the composition has been demolded. The moulds can also be dishes or pots which remain connected to the composition once manufactured so as to be subsequently placed in the housing of an item of packaging.

When the slurry is liquid, it can be injected via the bottom of the mould or be cast by simply filling the mould via its top opening. A process of injection via the bottom of the moulds is, for example, known as "back injection machine" or BIM filling. A process of filling of the moulds which consists in pouring the slurry into the mould from above is known as "top fill".

The slurry may also be more viscous, so that it is possible to meter-out said slurry by preparing pieces of slurry. The percentage of volatile liquid is preferably chosen such that the paste has a consistency that is sufficient for it to be possible for said slurry to be kneaded, metered-out and cut up. In this case, it is necessary to give the slurry its form such that the composition hugs the pot edges, before removing the volatile liquid. This forming can be carried out by pressing at the same time as the removal of the volatile liquid.

The preparation process according to the invention comprises a step of removing the volatile liquid, also called drying, of which the objective is to substantially remove the volatile liquid in order to solidify the composition.

The removal of the volatile liquid can be carried out with mechanical means such as suction, or thermal means such as heat.

Those skilled in the art will be able to adjust the drying time necessary in order to optimize the removal of the volatile liquid. The slurry may comprise a more or less high proportion of volatile liquid according to the removal time and means used.

The powder-based composition obtained by means of the process of the invention may comprise traces of volatile liquid used for preparing the slurry. This proportion is preferably less than 2% by weight, more preferably less than 1% by weight, relative to the total weight of the composition. The intention is generally to reduce as much as possible the proportion of residual volatile liquid in the final composition. The powder-based composition of the invention can be described as a "dry" powder, given the very low residual amount of volatile liquid used for its preparation.

The drying may comprise a step consisting in exposing the slurry to a stream of air of which the temperature is about 20 to 25° C., to infrared radiation, to microwave radiation, or in an oven.

The drying may also comprise a step of heating in an oven adjusted to a temperature ranging from 30 to 70° C., preferably ranging from 40 to 60° C. Usually, the drying of the composition may be complete after a period ranging from four to ten hours under these conditions. The pressure in the oven is preferably atmospheric pressure, and the humidity level in the oven is preferably controlled at between 70% and 90% relative humidity.

The drying can also be carried out by pressing, by suction, by gravity by overturning the moulds containing the slurry, by centrifugation, or by application of an absorbent material forming a blotter on the free surface of the slurry which has been poured into the moulds.

According to one embodiment, the drying comprises a step of drying by pressing and suctioning off the volatile liquid under vacuum, at ambient temperature (approximately 25° C.). The pressing is carried out by means of a stamp which comes into contact with the slurry and which compresses the composition between the bottom of the mould and its surface during the suctioning off.

The end of the stamp or the bottom of the mould is perforated so as to allow the volatile liquid to be extracted out of the slurry during the suctioning off.

The suctioning off is generally carried out in two steps, a first series of pressings carried out by means of a first stamp, each pressing being performed at a suctioning pressure $P1$ for a time $T1$ so as to initiate the removal of the liquid, followed by a second series of pressings carried out by means of a second stamp, which may be identical to or different from the first stamp, each pressing of said second series being performed at a suction pressure $P2$ greater than $P1$, for a time $T2$ greater than $T1$, in such a way as to continue the suctioning off of the liquid until a surface finish faithful to said second stamp is obtained. This suctioning off, preferably carried out in two steps, makes it possible to improve the surface finish of the cosmetic composition by preventing the formation of cracks or irregularities that may occur during the removal of the volatile liquid. A series of pressings within the meaning of the invention comprises at least one pressing by means of a press.

One of the objectives of the pressing—suctioning-off operation described above is a forming of the powder, without however being a compacting. The pressures used are consequently relatively mild. The suctioning pressure $P1$ is preferably about 0.05 to 0.3 MPa, while the suctioning pressure $P2$ is preferably about 0.3 to 0.8 MPa.

The following are, for example, carried out:
a first step comprising at least two presses for a respective period of from 1 to 10 seconds, typically 5 seconds, at a first pressure, generally of about 0.05 to 0.3 MPa, typically of about 0.1 MPa, in order to begin the removal of the volatile liquid, then
a second step comprising at least one press for a period of from 5 to 20 seconds, typically 10 seconds, at a second pressure, generally of about 0.3 to 0.8 MPa, typically of about 0.5 MPa.

In this embodiment, a porous material may be deposited at the free surface of the slurry in each mould, or be placed on the stamp which acts as a press, in order to retain the powder in the mould during the suctioning off. This porous material is, for example, an absorbent cloth, weft or sheet. This is removed from the composition once the suctioning off is complete.

The removal of the volatile liquid may also comprise the combination of the means described above. Thus, in accordance with a variant of the process of the invention, the removal of the volatile liquid contained in the slurry comprises a mechanical removal followed by a thermal removal. The process may comprise, for example, two successive steps: partial drying of the slurry using mechanical removal means so as to obtain a wet powder, and drying of the wet powder by thermal means. The mechanical removal can be carried out by suctioning off under a press, and the thermal removal can be carried out, for example, by drying in an oven, preferably at a temperature of less than 70° C., more preferably less than 60° C.

According to one preferred embodiment, the compositions of the invention are prepared by means of a process which comprises:
preparing the slurry,
introducing the slurry into a mould, for example by means of a pump and of an injection unit which advantageously comprises nozzles for injecting the slurry from below or above the moulds,
depositing a porous material at the free surface of the slurry,
placing the filled moulds under vacuum and removing the volatile liquid present in the paste by suctioning off, and preferably maintaining the slurry under a press during the suctioning off, and
returning to atmospheric pressure.

The moulds can then be oven-dried at atmospheric pressure with a controlled humidity level, according to the oven-drying conditions described above.

According to a second preferred embodiment, the slurry is spread on a plate, and then oven-dried at a controlled humidity level. The removal of the volatile liquid can be followed by screening. The loose powder obtained can be placed on sale after having been placed in packagings, such as bottles which have an applicator rigidly connected to the cap or the stopper. According to this process, loose powders for the face (powder foundation, blusher or face powder) or for the eyes (eye shadows) may be prepared.

According to a third embodiment of the process of the invention, the volatile liquid in the slurry is removed in order to obtain a dry powder, which is subsequently screened and then compacted. The compacting is carried out under the conventional conditions known to those skilled in the art, either directly in a packaging into which the dry powder has been poured, or in a dish which will subsequently be placed in a casing.

Once the composition has been dried in the mould, it can be demolded and handled in order to be placed in the packaging intended for sale. The mould may also be a pot or a dish that will subsequently be snap-fastened into or placed in the packaging without it being necessary to demold the composition.

The compositions of the invention make it possible to solve the stated technical problems. The present invention is particularly suitable for preparing cosmetic compositions intended for body and/or face care or makeup.

The process of the invention makes it possible to prepare a homogeneous powder in which the various components are well dispersed. The dispersion of the various ingredients in the powder obtained according to this process is in fact better than that of the powders obtained by means of a prior art process which uses the dry process.

The compositions of the invention exhibit in particular very good performance levels in terms of especially water resistance and of staying-power on the skin of the face, in particular the eyelids.

These compositions are therefore particularly suitable for preparing cosmetic body or face care and/or makeup compositions.

The present invention therefore relates to a cosmetic care and/or makeup method comprising the application of the power-based composition to at least one part of the skin.

Other purposes, characteristics and advantages of the invention will become clearly apparent to those skilled in the art following the reading of the explanatory description which makes reference to examples that are given only by way of illustration and that can in no way limit the scope of the invention.

The examples form an integral part of the present invention and any characteristic which appears to be novel over any prior art on the basis of the description taken as a whole, including the examples, forms an integral part of the invention in terms of its function and in terms of its generality. Thus, each example has a general scope.

Furthermore, in the examples, all the percentages are given by weight, unless otherwise indicated, and the temperature is expressed in degrees Celsius unless otherwise indicated, and the pressure is atmospheric pressure unless otherwise indicated. The names of the chemical products correspond to their INCI name or to their chemical name according to the rules of nomenclature of the IUPAC.

Example 1

Compact-Powder Eyeshadow

Compact eyeshadows having the following composition were produced:

| Phase A | |
| --- | --- |
| TALC | Qs 100 |
| SORBIC ACID | 0.3 |
| IRON OXIDE CI 77499 | 13.2 |
| Phase B | |
| MICA/SILICA/TITANIUM DIOXIDE CI 77891 | 5.0 |
| MICA/IRON OXIDE CI 77491 | 7.0 |
| Phase C | |
| PENTYLENE GLYCOL | 2.5 |
| PHENOXYETHANOL | 0.9 |
| Ammonia acryloyldimethyltaurate/VP copolymer | 0.2 |
| OCTYLDODECYL STEAROYL STEARATE | 20.0 |

Preparation of the Slurry

The ingredients of phase A were mixed in a Lödige or Waring mixer for 10 to 30 minutes. The ingredients of phase B were added to the mixer and mixed with phase A for at least 5 minutes.

In a Rayneri mixer, the ingredients of phase C were mixed with purified water in order to prepare an emulsion in which the water represents 50% by weight of the weight of the emulsion.

The mixture of phases A and B was poured, with stirring, into the Rayneri mixer containing the emulsion. The slurry was kneaded for 10 to 30 minutes. If necessary, water was added in order to adjust the consistency of the slurry. The slurry was smoothed for a further 5 to 10 minutes if necessary, in order to be sure that the slurry was homogeneous.

Moulding of the Powders

The slurry was placed in a kneading machine and worked into the form of tubes, and then cut up so as to be placed in pots. The drying was carried out by suctioning off the volatile liquid under vacuum, with the following being successively applied:

- two presses, for a period of 5 seconds, at a pressure of 0.1 MPa, in order to begin the suctioning off of the volatile liquid, then
- one press, for a period of 10 seconds, at a pressure of 0.5 MPa.

A cloth was placed on the head of each stamp so that it did not come into direct contact with the slurry.

The filled and pressed pots were subsequently placed in an oven adjusted to a temperature of 50° C., for a period of 5 hours, at atmospheric pressure, and at a humidity level of 80%.

Mechanical Impact Resistance Test

Drop tests were carried out on the compact powders previously prepared according to the following protocol. The percentage of block copolymer (ammonium acryloyldimethyltaurate/VP copolymer) was varied by adjusting the percentage of OCTYLDODECYL STEAROYL STEARATE binder, without varying the proportions of the other ingredients of the formulation.

The protocol that was followed in order to define the drop strength of the compact powders consists in

- standing over a bench and holding a 30 cm graduated ruler vertically in one hand;
- holding the pot horizontally in the other hand—the bottom of the pot downwards—above the bench;
- letting go of the pot and recommencing the operation until the appearance of the first crack or break, and noting the number of drops performed;
- repeating the operation on at least two or three pots, and then calculating the mean of the results.

| % Block | Number of drops | | |
|---|---|---|---|
| copolymer | 24 hours° | 21 days° | mean |
| 0% | 2, 3 | 4, 3, 3 | 3 |
| 0.1% | 7, 7 | 4, 2, 5 | 5 |
| 0.2% | 9, 10 | 9, 17, 10 | 11 |
| 0.4% | 15, 44 | 19*, 20*, 22 | 24 |

*complete detachment of the block
°after moulding of the powders

The block copolymer very clearly improves the mechanical impact resistance of the compact powders.

Example 2

Compact-Powder Eyeshadow

Compact eyeshadows having the following composition were produced:

| Phase A | |
|---|---|
| TALC | Qs 100 |
| SORBIC ACID | 0.3 |
| IRON OXIDE CI 77499 | 1.0 |
| MAGNESIUM MYRISTATE | 2.0 |
| Phase B | |
| MICA/TITANIUM DIOXIDE CI 77891 | 30 |
| SILICA/ALUMINA | 5.0 |
| MICA/TITANIUM DIOXIDE CI 77891/FERRIC FERROCYANIDE | 0.5 |
| MICA/IRON OXIDE CI 77491 | 0.5 |
| Phase C | |
| PENTYLENE GLYCOL | 2.5 |
| PHENOXYETHANOL | 0.9 |
| Ammonium acryloyldimethyltaurate/VP copolymer | 0.2 |
| OCTYLDODECYL STEAROYL STEARATE | 22.0 |

Preparation of the Slurry
It was carried out according to the protocol in Example 1.
Moulding of the Powders
It was carried out under the same conditions as those of Example 1.
Mechanical Impact Resistance Test
It was carried out under the same conditions as those of Example 1.

| % Block | Number of drops | | |
|---|---|---|---|
| copolymer | 24 hours° | 21 days° | mean |
| 0% | 2, 2 | 4, 4, 7 | 3 |
| 0.1% | 10, 8 | 8*, 8*, 10 | 8 |
| 0.2% | 6, 7 | 9*, 11, 10 | 8 |
| 0.4% | 14*, 14* | 13*, 16*, 15* | 14 |

*complete detachment of the block
°after moulding of the powders

The block copolymer very clearly improves the mechanical impact resistance of the compact powders.

Example 3

Compact-Powder Eyeshadow

Compact eyeshadows having the following composition were produced:

| Phase A | |
|---|---|
| TALC | Qs 100 |
| SORBIC ACID | 0.3 |
| IRON OXIDE CI 77499 | 25 |
| Phase B | |
| FERRIC FERROCYANIDE/MICA/IRON OXIDE CI 77491/TITANIUM DIOXIDE CI 77891 | 5.0 |
| IRON OXIDE CI 77499/MICA/TITANIUM DIOXIDE CI 77891 | 25.0 |
| IRON OXIDE CI 77491/MICA | 5.0 |
| Phase C | |
| PENTYLENE GLYCOL | 2.5 |
| PHENOXYETHANOL | 0.9 |
| Ammoniun acryloyldimethyltaurate/VP copolymer | 0.2 |
| OCTYLDODECYL STEAROYL STEARATE | 20.0 |

Preparation of the Slurry
It was carried out according to the protocol of Example 1.
Moulding of the Powders
It was carried out under the same conditions as those of Example 1.
Mechanical Impact Resistance Test
It was carried out under the same conditions as those of Example 1.

| % Block | Number of drops | | |
|---|---|---|---|
| copolymer | 24 hours° | 21 days° | mean |
| 0% | 3, 5 | 2, 6, 6 | 4 |
| 0.1% | 5, 8* | 7, 5, 7 | 6 |
| 0.2% | 6, 16*, 20 | 17*, 15, 15 | 17 |
| 0.4% | 15*, 42 | 22*, 14, 20* | 22 |

*complete detachment of the block
°after the moulding of the powders

The block copolymer very clearly improves the mechanical impact resistance of the compact powders.

Example 4

Compact-Powder Foundation

A compact foundation having the following composition was produced:

| Phase A | |
|---|---|
| TALC | Qs 100 |
| TETRASODIUM EDTA | 0.2 |
| IRON OXIDE/DIMETHICONE | 4.3 |
| TITANIUM DIOXIDE/DIMETHICONE | 3.7 |
| Phase B | |
| HDI/TRIMETHYLOL HEXYLLACTONE CROSSPOLYMER (PLASTIC POWDER ® D-400) | 4.6 |
| METHYL METHACRYLATE CROSSPOLYMER (COVABEAD ® LH 170) | 23.1 |
| Phase C | |
| PHENOXYETHANOL | 0.4 |
| GLYCEROL | 7.0 |
| Ammonium acryloyldimethyltaurate/VP copolymer | 0.4 |

Preparation of the Slurry
It was carried out according to the protocol of Example 1.
Moulding of the Powders
The slurry was placed in a kneader and worked into the shape of tubes, which were placed in pots. The drying was carried out by suctioning off the volatile liquid under vacuum, with the following being successively applied:
- a press, for a period of 5 seconds, at a pressure of 0.1 MPa, in order to begin the suctioning off of the volatile liquid, then
- a press, for a period of 10 seconds, at a pressure of 0.5 MPa.

A cloth was placed over the head of each stamp so that it did not come into direct contact with the slurry.

The filled and pressed pots were subsequently placed in an oven adjusted to a temperature of 50° C., for a period of 5 hours, at atmospheric pressure, and at an 80% humidity level.

Example 5

Compact-Powder Eyeshadow

A compact eyeshadow was prepared by producing a slurry having the following composition:

| Phase A | |
|---|---|
| TALC | Qs 100 |
| MICA/LAUROYLLYSINE | 30.0 |
| MAGNESIUM STEARATE | 1.9 |
| NYLON-12 | 4.9 |
| MANGANESE VIOLET | 3.0 |
| IRON OXIDES | 21.9 |
| TITANIUM DIOXIDE | 0.5 |
| Phase B | |
| PHENOXYETHANOL | 0.8 |
| HYDROGENATED POLYISOBUTENE | 4.5 |
| Ammonium acryloyldimethyltaurate/VP copolymer | 0.1 |

Phase A was mixed in a Lödige device for 10 to 15 minutes. Phase B was prepared and mixed with phase A according to the protocol described for phase C in Example 1. Water represented 43% by weight of the weight of the slurry.

The slurry was layered onto a plate and placed in an oven adjusted to a temperature of 50° C., for a period of 5 hours, at atmospheric pressure, and at an 80% humidity level.

The powder obtained was screened, placed in pots, and then compacted.

Example 6

Loose Powder Eyeshadow

An eyeshadow in the form of a loose powder having the following composition was prepared:

| Phase A | |
|---|---|
| TALC | Qs 100 |
| MICA/LAUROYLLYSINE. | 30.3 |
| MAGNESIUM STEARATE | 1.9 |
| NYLON-12 | 5.0 |
| MANGANESE VIOLET | 3.0 |
| IRON OXIDES | 22.2 |
| MICA/TITANIUM DIOXIDE CI | 0.5 |

| -continued | |
|---|---|
| 77891/IRON OXIDE CI 77492 | |
| SORBIC ACID | 0.3 |
| TITANIUM DIOXIDE | 0.5 |
| Phase B | |
| PHENOXYETHANOL | 1.1 |
| PENTYLENE GLYCOL | 2.5 |
| Ammonium acryloyldimethyltaurate/VP copolymer | 0.05 |

The slurry was prepared according to the protocol of Example 5. The powder obtained was subsequently screened and packaged.

The invention claimed is:

1. Process for manufacturing a solid anhydrous cosmetic compact powder, comprising:
   (a) from 70% to 99% by weight of at least one particulate solid phase made of pigments and fillers,
   (b) from 0.1% to 30% by weight of at least one non-volatile liquid phase comprising an oil, an alcohol chosen from C3-C5 polyols, glycol ethers, and mixtures thereof, and
   (c) from 0.01% to 4% by weight of at least one block copolymer obtained from a first monomer of 2-acrylamidomethylpropanesulphonic acid or a salt thereof, and from a vinyl second monomer having a nitrogenous side chain,
said process comprising:
   (i) mixing the particulate solid phase, the non-volatile liquid phase, the block copolymer and water so as to obtain a homogenous slurry,
   (ii) placing the slurry in a mould, and
   (iii) removing water present in the slurry, wherein
the slurry is devoid of a surfactant, and
said pigments and fillers are devoid of surface treatment that renders them hydrophobic or hydrophilic.

2. Process according to claim 1, wherein the composition is not demolded after the removal of the water.

3. Process according to claim 1, wherein the removal of the water is carried out in two successive steps: a mechanical removal so as to obtain a wet powder, and drying of the wet powder by a thermal process.

4. Process according to claim 1, wherein the step of removing water is carried out by suctioning off under a press, and then by drying in an oven at a temperature of less than 60° C.

5. Process according to claim 4, wherein the suctioning off under a press is carried out in two steps, a first series of pressings carried out with a first stamp, each pressing being performed at a pressure P1 of between 0.05 and 0.3 MPa for a time T1 so as to initiate the removal of the liquid, followed by a second series of pressings carried out with a second stamp, each pressing of said second series being performed at a pressure P2 of between 0.3 and 0.8 MPa for a time T2 greater than T1, in such a way as to continue the removal of the liquid until a surface finish faithful to the second stamp is obtained.

6. Process according to claim 1, wherein the block copolymer is Sodium Acryloyldimethyltaurate/VP Crosspolymer, or Ammonium Acryloyldimethyltaurate/VP Copolymer.

* * * * *